(12) United States Patent
Martin et al.

(10) Patent No.: US 11,615,885 B2
(45) Date of Patent: Mar. 28, 2023

(54) WEARABLE SENSING DEVICE AND SENSOR UNIT FOR ACQUIRING ONE OR MORE PHYSIOLOGICAL SIGNALS OF A SUBJECT

(71) Applicant: Onera Technologies B.V., Eindhoven (NL)

(72) Inventors: Ruben de Francisco Martin, Leuven (BE); Peter Cramer, Leuven (BE); Bastiaan Pieter Hemmes, Leuven (BE)

(73) Assignee: Onera Technologies B.V., Eindhoven (NL)

( * ) Notice: Subject to any disclaimer, the term of this patent is extended or adjusted under 35 U.S.C. 154(b) by 737 days.

(21) Appl. No.: 16/488,095

(22) PCT Filed: Feb. 22, 2018

(86) PCT No.: PCT/EP2018/054436
§ 371 (c)(1),
(2) Date: Aug. 22, 2019

(87) PCT Pub. No.: WO2018/154016
PCT Pub. Date: Aug. 30, 2018

(65) Prior Publication Data
US 2019/0378615 A1    Dec. 12, 2019

(30) Foreign Application Priority Data
Feb. 25, 2017  (EP) .................................... 17158012

(51) Int. Cl.
*A61B 5/00* (2006.01)
*G16H 40/67* (2018.01)
*G06F 1/16* (2006.01)

(52) U.S. Cl.
CPC ........... *G16H 40/67* (2018.01); *A61B 5/6833* (2013.01); *G06F 1/163* (2013.01)

(58) Field of Classification Search
CPC ...... G16H 40/67; A61B 5/6833; A61B 5/282; A61B 5/053; A61B 5/389;
(Continued)

(56) References Cited

U.S. PATENT DOCUMENTS

| | | | | |
|---|---|---|---|---|
| 2012/0306662 A1* | 12/2012 | Vosch | ...................... | H04Q 9/00 340/870.07 |
| 2014/0094676 A1* | 4/2014 | Gani | ...................... | A61B 5/332 600/386 |

(Continued)

FOREIGN PATENT DOCUMENTS

WO    2008068695 A1    6/2008

OTHER PUBLICATIONS

International Search Report for International Application No. PCT/EP2018/054436, dated Apr. 24, 2018 (4 pages).
(Continued)

*Primary Examiner* — Michael A Keller
(74) *Attorney, Agent, or Firm* — Kagan Binder, PLLC

(57) ABSTRACT

A wearable sensing device (100) for sensing one or more physiological signals of a subject, comprising: a sensor unit (200), including a housing, a connection receptacle (210) and electronic circuitry configured for acquiring one or more physiological signals received via the connection receptacle; a patch unit (300), including a connection plug (310) connected via conductive tracks (341) to a plurality of electrodes (342) configured for sensing the one or more physiological signals. The connection plug (310) is configured for being connectable with the connection receptacle (210) such that the one or more physiological signals sensed by the electrodes (342) are transmitted to the electronic circuitry of the sensor unit (200). The patch unit (300) comprises at least one top layer (380) and at least one bottom layer (360, 330), each including an adhesive material, such that the at least
(Continued)

one top layer (380) is configured to be attachable to a surface of the housing and the at least one bottom layer (360, 330) is configured to be attachable to the skin of the subject.

13 Claims, 15 Drawing Sheets

(58) Field of Classification Search
CPC .... A61B 2560/0285; A61B 2560/0443; A61B 2560/045; A61B 2562/227; G06F 1/163
See application file for complete search history.

(56) References Cited

U.S. PATENT DOCUMENTS

| 2015/0094558 | A1* | 4/2015 | Russell | G16H 40/67 |
| | | | | 600/386 |
| 2016/0242654 | A1 | 8/2016 | Quinlan et al. | |
| 2017/0164878 | A1* | 6/2017 | Connor | G09B 19/00 |

OTHER PUBLICATIONS

Written Opinion for International Application No. PCT/EP2018/054436, dated Apr. 24, 2018 (7 pages).

\* cited by examiner

1A

1B

1C

1D

1E

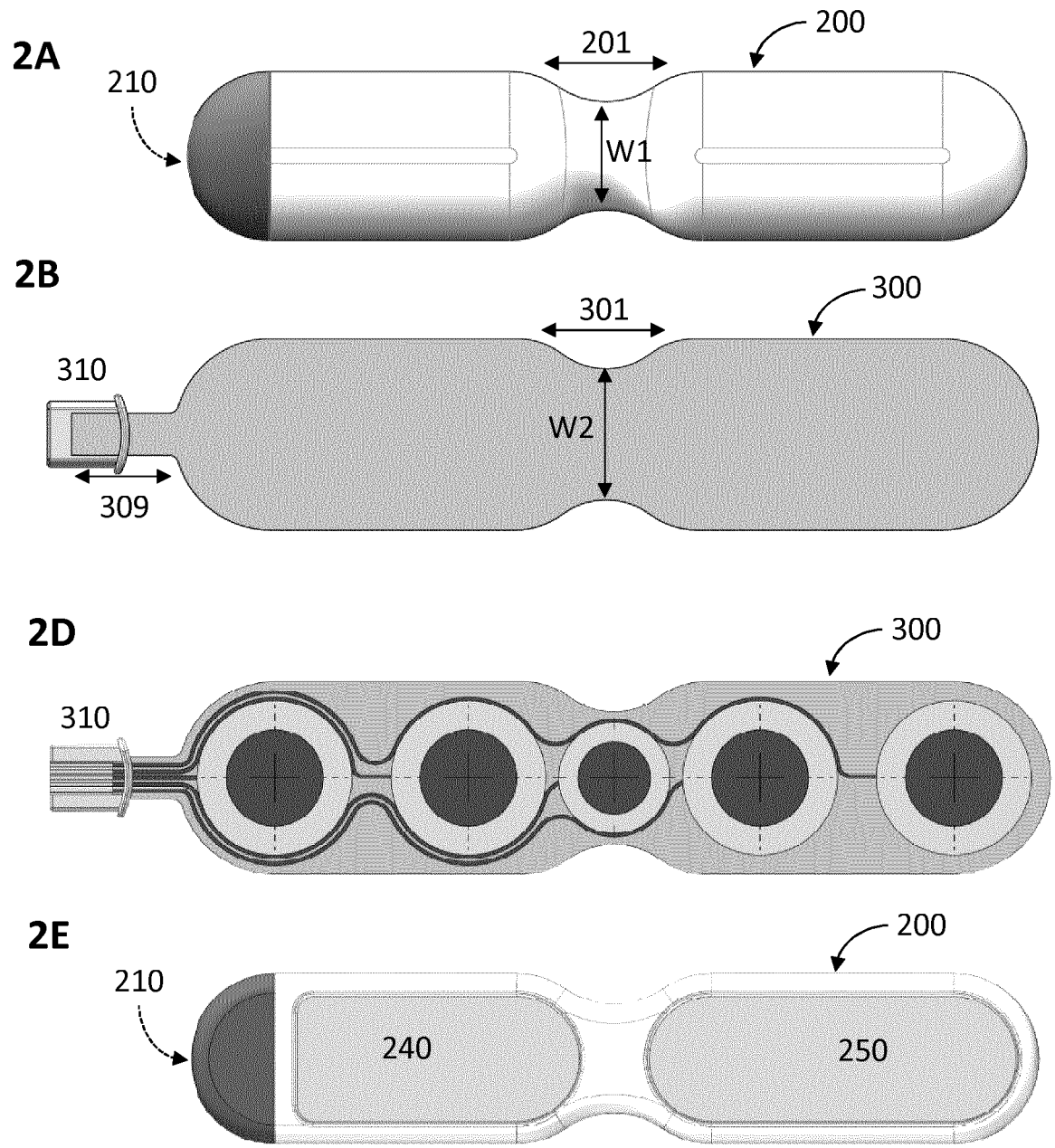

Figure 3 (continuation)
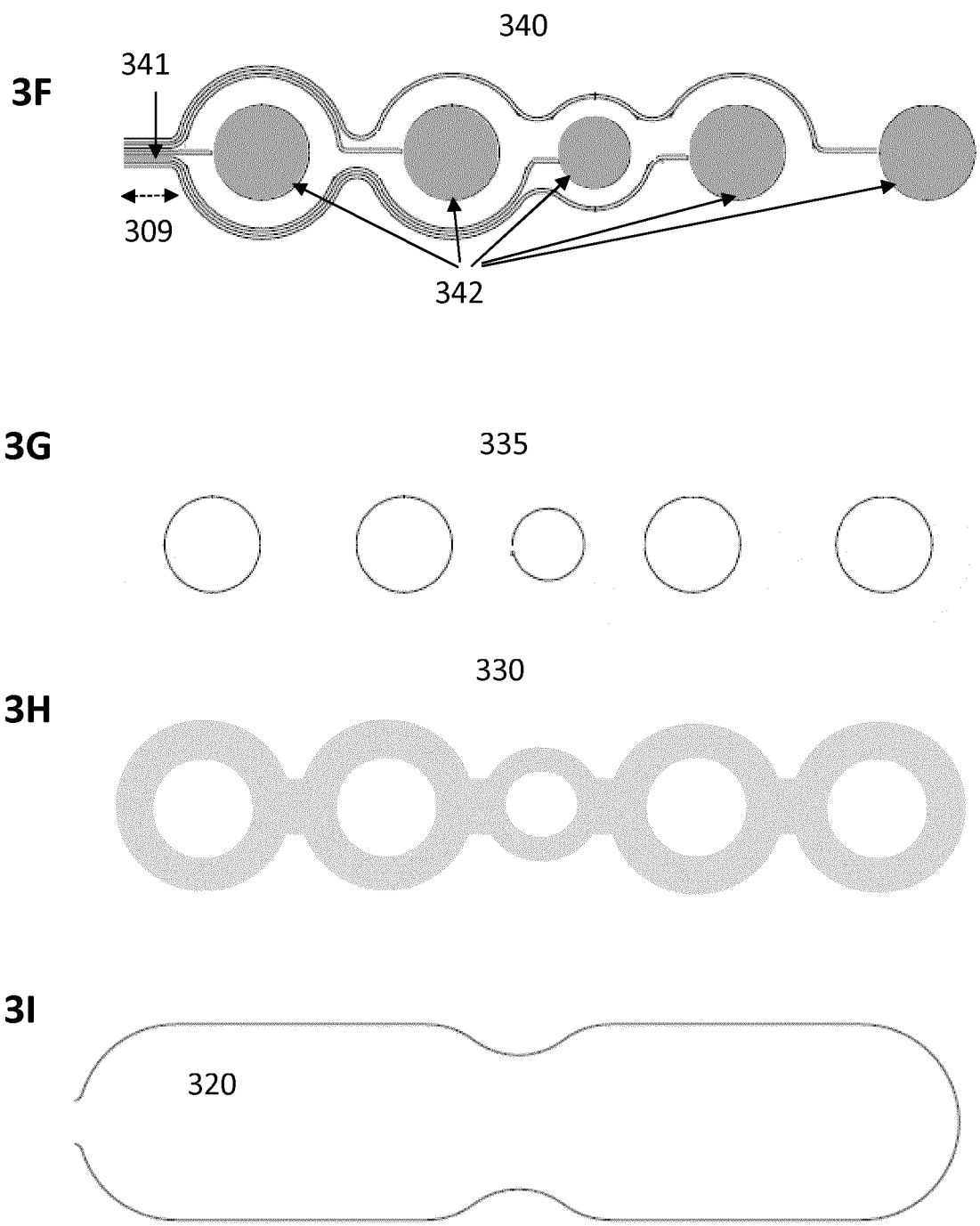

6A

6B  6C

6D

6E

8A

WEARABLE SENSING DEVICE AND SENSOR UNIT FOR ACQUIRING ONE OR MORE PHYSIOLOGICAL SIGNALS OF A SUBJECT

CROSS-REFERENCE TO RELATED APPLICATIONS

This application claims priority to International Application No. PCT/EP2018/054436, filed Feb. 22, 2018 and titled "WEARABLE SENSING DEVICE AND SENSOR UNIT FOR ACQUIRING ONE OR MORE PHYSIOLOGICAL SIGNALS OF A SUBJECT," which in turn claims priority from a European Application having ser. no. 17158012.9, filed Feb. 25, 2017, titled "WEARABLE SENSING DEVICE AND SENSOR UNIT FOR ACQUIRING ONE OR MORE PHYSIOLOGICAL SIGNALS OF A SUBJECT," both of which are incorporated herein by reference in their entireties.

TECHNICAL FIELD

The present description relates to non-invasive biosignal activity measurement, acquisition or monitoring sensors and systems, including for example, biopotential and/or bio-impedance signal acquisition systems and devices, and more specifically to wearable sensing devices and sensor units for acquiring one or more physiological signals of a subject.

BACKGROUND

There is currently an interest for the development of portable, lightweight an non-invasive biosignal activity measurement and acquisition systems. Portable and wearable systems for biopotential monitoring have been developed to provide monitoring of various health-related parameters during everyday life, such as electrocardiography (ECG) systems and electromyography (EMG) systems. A prior art ECG system typically includes a number of electrodes which are adhesively attached to the skin of the wearer. For an ECG system the electrodes are typically attached to the chest region of the wearer. A detector unit for receiving and processing the signals from the electrodes may be connected to each of the electrodes by lead wires suspended between the attachment points at an electrode and at the control unit. The detector unit may in turn be carried by the user by means of a strap or a necklace. Alternatively, the ECG system may be implemented as an adhesive patch structure including both the detector unit and a number of electrodes. Conductive paths for connecting the electrodes to the detector unit are integrated in the patch structure. The adhesive patch structure is generally formed as a single piece of plastic material with an adhesive configured to be attached to the body.

There is a need to improve state of the art wearable sensing devices for sensing one or more physiological signals of a subject.

SUMMARY

The invention is defined by the claims.

The present description provides for a new and advantageous wearable sensing device and sensor unit for acquiring a biosignal activity of a subject, for example, one or more physiological signals of a subject, including but not limited to, electrocardiogram, electromyogram and/or bioimpedance signals.

According to an example embodiment, there is provided a wearable sensing device for one or more physiological signals of a subject, comprising: a wearable sensor unit which includes a housing, a connection receptacle and electronic circuitry configured for acquiring and/or processing one or more physiological signals received via the connection receptacle; and a wearable patch unit which includes a connection plug connected via conductive tracks to a plurality of electrodes configured for measuring the one or more physiological signals; and wherein the connection plug is configured for being connectable with the connection receptacle such that the one or more physiological signals measured by the electrodes are transmitted to the electronic circuitry of the sensing unit, and the patch unit comprises at least one top layer and at least one bottom layer, each including an adhesive material, such that the at least one top layer is configured to be attachable to one or more of the housing surfaces and the at least one bottom layer is configured to be attachable to the skin of the subject.

According to an example embodiment, the wearable sensing device is easy to use and/or mount and apply on the body. Also advantageously, according to an example embodiment, the wearable sensing device is comfortable to wear. Also advantageously, according to an example embodiment, the wearable sensing device comprises a disposable patch unit and a reusable sensor unit that is furthermore easy to maintain and recharge. Also advantageously, according to an example embodiment, the wearable sensing device is cheap and/or cost-efficient. According to an example embodiment, advantageously, the cost of the patch unit can be minimized and higher cost electronic components may be included in the reusable sensor unit (the housing with sensing electronic circuitry). Also advantageously, according to an example embodiment, the wearable sensing device provides increased signal quality acquisition, e.g. by reducing, for example, motion artifacts. It is also advantageous that the wearable sensing device according to example embodiments has a comfortable shape, is flexible, clean and/or easy to handle and attach.

According to an example embodiment, the wearable sensing device may be applied or attached to the chest, the side or torso of a person. According to an example embodiment, the wearable sensing device may capture ECG and/or bio-impedance signals from a person. According to an example embodiment, the wearable sensing device may also comprise motion sensors and capture ECG, bio-impedance and motion from a person. According to an example embodiment, the wearable sensing device may be advantageously used to extract information related to respiration, sleep and/or sleep staging of a person. According to an example embodiment, the acquired physiological information is stored on the device and/or transmitted to a mobile phone for further processing and to display it to the user.

According to an example embodiment, there is provided a wearable sensor unit for one or more physiological signals of a subject, comprising: a housing; a connection receptacle; and electronic circuitry configured for acquiring and/or processing one or more physiological signals received via the connection receptacle; and wherein the sensing unit is further configured such that the housing comprises a surface to be fixedly attachable to a patch unit; the connection receptacle is arranged for receiving a connection plug and signals from said patch unit; and the electronic circuitry is arranged for acquiring one or more physiological signals received via the connection receptacle and originating from a plurality of electrodes for sensing the one or more physiological signals in said patch unit.

According to an example embodiment, the wearable sensor unit is advantageously light-weight and can be carried by the subject without effort or burden in his or her day to day life. Furthermore, the light-weight wearable sensor unit reduces motion artifacts that deteriorate signal quality acquisition. According to an example embodiment, the wearable sensor unit comprises a housing, made of, for example, plastic and/or rubber. The housing includes and provides protection for the circuit electronics and the battery. According to an example embodiment, the housing may comprise two different sections or segments, e.g. one four housing the electronics and one for housing the battery, connected by a middle section. According to an example embodiment, the two housing segments may be made of plastic and the middle mechanically connecting housing section may be made of a more flexible material, such as rubber, thereby improving portability or user comfort when attached to the body. According to an example embodiment, the battery powers the circuit electronics and is connected with wires. According to an example embodiment, the circuit electronics include, for example, an acquisition circuit that acquires the physiological signals captured by electrodes in the patch, digitizes the signals, provides local data storage, local processing and may also be configured for wireless transmission to an external device, such as a mobile phone or mobile computing unit. According to an example embodiment, the circuit electronics is configured to measure bio-impedance, ECG, and also motion from an accelerometer. According to an example embodiment, the sensor unit comprises a receptacle connection or socket for receiving the biosignals from the disposable patch and such that the circuit electronics can process those signals. According to an example embodiment, the patch unit comprises a connector or plug that is configured to be connected with the receptacle or socket of the sensor unit. According to an example embodiment, the receptacle and the plug are implemented following a Micro-USB standard. According to an example embodiment, the patch unit plug may be implemented in a Micro-USB-like or compatible standard manner but deviating from standard materials used. According to an example embodiment, the sensor unit may comprise two connecting receptacles or sockets, one for receiving the patch unit plug and another for receiving an USB plug for battery re/charging purposes. According to an example embodiment, the sensor unit may comprise just one socket for both connecting the circuit electronics in the sensor unit to the patch and for recharging the sensor unit battery. In this way, patient safety is increased as it ensures that the user is not able to recharge the sensor unit while wearing it. Furthermore, the fact that the sensor unit can be easily detached from the patch unit allows for easy recharging of the sensor unit with a conventional USB or Micro-USB connection, while not in use. According to an example embodiment, the patch unit may comprise two or more electrodes for measuring ECG and bioimpedance signals. According to an example embodiment, the patch unit may comprise three electrodes, for example, including an additional bias electrode. When the receptacle and plug are implemented following the Micro-USB standard, only two pins are used for VCC and GND when charging the sensor unit, while the other three lines remain unused. When connecting a disposable patch to the socket, the remaining three lines are used for data acquisition from three electrodes (if a bias electrode is used) or from two electrodes (if no bias electrode is used). According to another example embodiment, the patch unit may comprise five electrodes, and in this case, the circuit electronics of the sensing unit comprises a voltage sensing circuit configured to detect whether a DC voltage level above a certain threshold is present between the VCC and GND pins. If the DC voltage level is above the threshold, then the circuit electronics is switched to charging mode and the VCC and GND pins in the USB micro socket are used for recharging of the battery. On the other hand, if the DC voltage level is below the defined threshold, then the circuit electronics is switched to acquisition mode and the five pins connected to the patch electrodes are used as inputs to the data acquisition system.

According to an example embodiment, the wearable patch unit is, advantageously, a disposable patch. According to an embodiment, the patch unit includes a foil substrate, such as PET or TPU, configured for receiving printed electrodes and conductive tracks, for example, by using conductive ink printing technology. According to an embodiment, the electrode tracks end in parallel so that a connector can be easily added or clamped at the end. According to an embodiment, the patch unit includes layers with adhesive properties both on an upper/top side and lower/bottom side of the patch. This advantageously allows the patch to both adhere to the subject when applying the lower/bottom side layer of the patch on the body skin, and to the housing when pressing the upper/top side layer of the patch on the housing surface or vice versa. In this way, the sensing device is easy to apply and the patch unit is properly attached to the housing (reduces movement artifacts when the patient wears the device). The layers with adhesive properties are protected, before use, by a liner. Just before operation, and for the purpose of attaching the patch to the sensor unit and the body skin, the user shall remove the protective liner from the top and bottom sides of the patch so that the adhesive layers can be used. According to an example embodiment, the patch unit also includes a conductive gel layer on the electrodes such that good conductivity properties between the electrode and the skin is ensured. According to an example embodiment, the patch unit comprises a substrate or non-conductive layer, such as a textile or plastic foil that provides support for the rest of the patch layers and for the connecting plug. The connecting plug of the patch unit may be placed on any of the sides of the patch. According to an example embodiment the plug is placed on a flexible strip that extends from a lateral of the patch. According to an example embodiment, the flexible strip is made of the same material and forms part of the patch substrate and/or foil layer. According to an example embodiment, the strip comprises electrode tracks, for example printed electrode tracks as part of the foil layer. According to an embodiment, such strip is defined, e.g. by dimensions and flexibility, so that it allows the plug, e.g. when the strip is bended, to enter the connection receptacle of the sensor unit. Advantageously, the strip reduces mechanical stress on the connection so that unwanted damage to the connector is reduced. According to an example embodiment, the connector or connection plug of the patch unit is implemented in the shape and form of Micro-USB standard plug. The connector plug however does not need to be metallic and may be made of low cost materials such as plastic or rubber. The printed electrode tracks coming out of the patch unit are built and configured in such a fashion that, when inserting this plug into a standard Micro-USB socket or receptacle, the pins are properly connected. The patch unit may comprise two or more electrodes. According to an example embodiment, the patch unit contains only two electrodes, which may be used, for example, for a bipolar bio-impedance and ECG measurement. According to an example embodiment, the patch unit contains three electrodes, that is, with an additional bias electrode in the middle. According to an embodiment, when implemented as a Micro-USB plug, the VCC and GND pins are not used, while the other three or any two of the remaining three pins are then used. According to an example embodiment, the patch unit comprises five electrodes, of which, for example, four are used for a tetrapolar bio-impedance measurement, and out of these four, two electrodes are used to measure ECG. The fifth electrode is a bias electrode located in the middle.

It shall be noted that the wearable sensing device according to the present description can be manufactured and made available as a kits of parts, that is, the sensor unit and the patch unit or even patch layers may be manufactured independently and sold as a kit in separate parts. It is only when the wearable sensor device is in operation, or applied on the body for biosignal acquisition purposes, that the parts shall be mounted together and cooperate to provide its function. In terms of operation and usage, that is, when the wearable sensing device shall be mounted or put together and applied to the body skin for biosignal activity monitoring, the user shall attach the housing of the sensor unit to the patch unit and the patch unit to the body skin. According to an example embodiment, a user first takes a patch unit and then connects that unit to the sensor unit via the connection plug. In a subsequent step, the user removes a first protective liner on the top part of the patch and bends the patch unit so that the patch's adhesive layer falls on the bottom surface part of the sensor unit's housing, and thereby the patch sticks to the sensor unit. In a next step, the user peels off a second protective liner from the bottom part of the patch unit and sticks the patch on the preferred body skin location, e.g. the chest, and the data acquisition starts (either automatically by "lead on" detection or based on a user action to start the recording). It shall be noticed that other ways of attaching and connecting the parts of the described wearable sensor device are possible and directly derivable. After use of the wearable sensing device, the user may take the patch off, turn the sensor unit off and/or unplug the patch. The user may dispose of the patch unit and maintain/reuse the sensor unit. The sensor unit can be used again, with a new disposable patch unit.

Certain objects and advantages of various new and inventive aspects have been described above. It is to be understood that not necessarily all such objects or advantages may be achieved in accordance with any particular embodiment of the present invention as described in the claims. Those skilled in the art will recognize that the solution as described in the claims may be embodied or carried out in a manner that achieves or optimizes one advantage or group of advantages without necessarily achieving other objects or advantages.

BRIEF DESCRIPTION OF THE DRAWINGS

The above and other aspects of the sensing device and sensing unit according to the present invention will be shown and explained with reference to the non-restrictive example embodiments described hereinafter.

FIG. 2A shows a top view of a wearable sensor unit according to another example embodiment.

FIG. 2B shows a top view of a wearable patch unit according to another example embodiment.

FIG. 2D shows a bottom view of a wearable patch unit according to another example embodiment, when the bottom protective liner is removed.

FIG. 2E shows a bottom view of a wearable sensor unit according to another example embodiment.

DETAILED DESCRIPTION

In the following, in the description of example embodiments, various features may be grouped together in a single embodiment, figure, or description thereof for the purpose of streamlining the disclosure and aiding in the understanding of one or more of the various inventive aspects. This is however not to be interpreted as the invention requiring more features than the ones expressly recited in the independent claims. Furthermore, combinations of features of different embodiments and obvious known alternative structural means are meant to be within the scope of the present description, as would be clearly understood and derived by those skilled in the art at the time of the invention. Additionally, in some examples, well-known methods, structures and techniques have not been shown in detail in order not to obscure the conciseness of the description.

Figure 1:
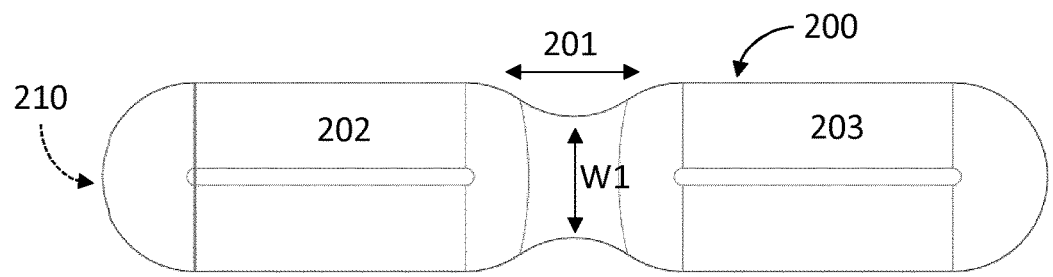
FIG. 1A shows a top view of a wearable sensor unit according to an example embodiment.
FIG. 1B shows a top view of a wearable patch unit according to an example embodiment.
FIG. 1C shows a side view of a wearable sensing device according to an example embodiment, when the patch unit is attached to the housing of the wearable sensor unit.
FIG. 1D shows a bottom view of a wearable patch unit according to an example embodiment, when the bottom protective liner is removed.
FIG. 1E shows a bottom view of a wearable sensor unit according to an example embodiment.
Figure 1:
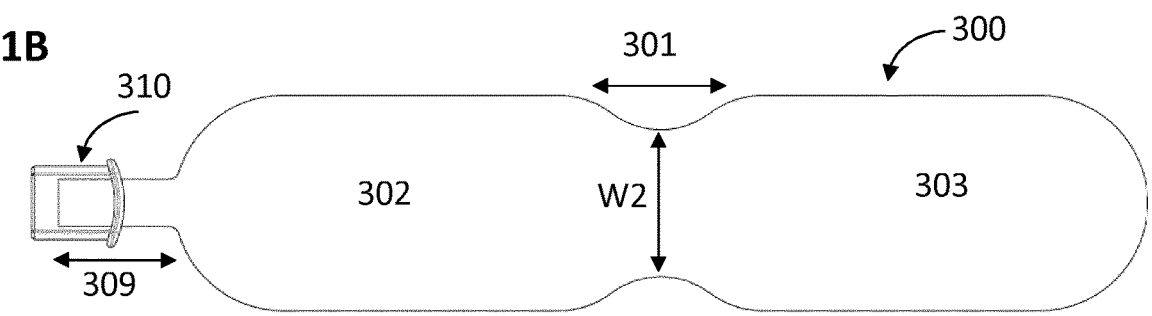
Figure 1:
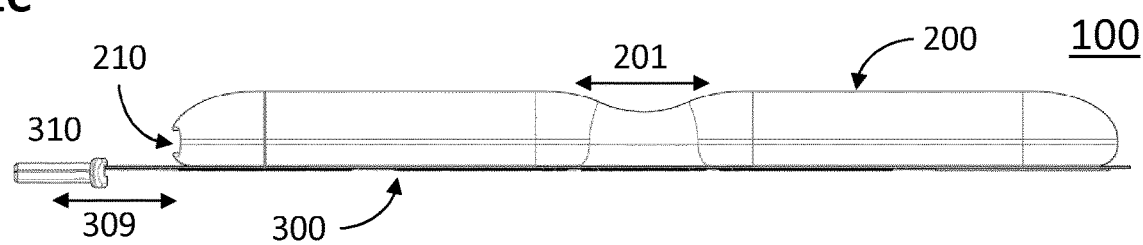
Figure 1:
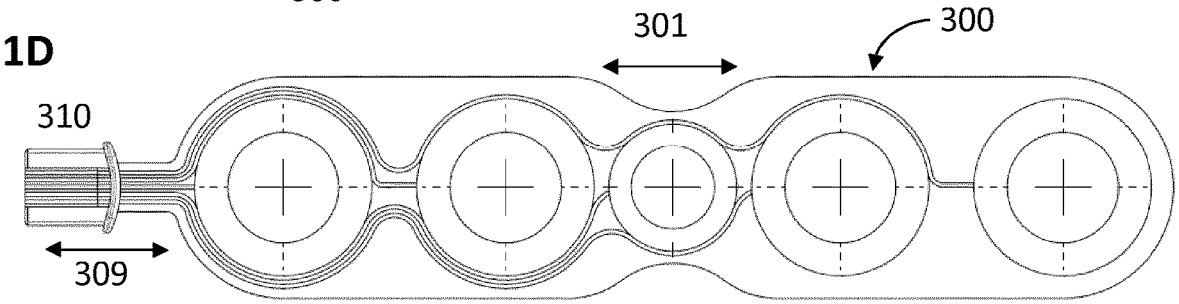
Figure 1:
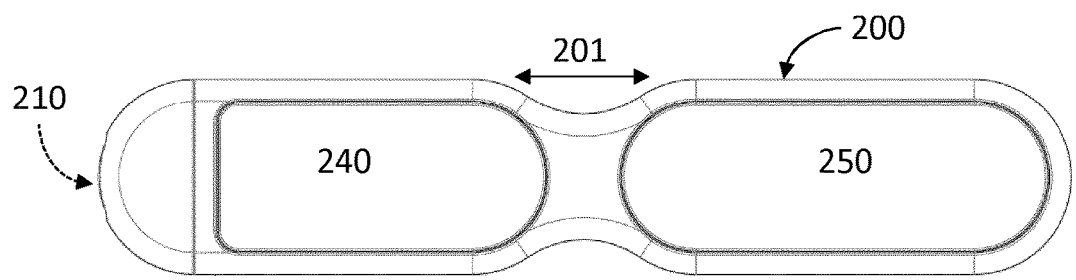

FIG. 1A shows a top view of a wearable sensor unit 200 according to an example embodiment, comprising a cover housing including a first segment 202, a second segment 203 and a segment connecting section 201, a connection receptacle or socket 210 (not shown directly in this figure), and electronic circuitry (not shown, within the housing) configured for acquiring and/or processing one or more physiological signals received via the connection receptacle. The housing may be made of, for example, plastic and/or rubber. The housing includes and provides protection for the circuit electronics and a power battery. According to an example embodiment, the housing may comprise at least two different sections or segments, a first and a second segment 202, 203, e.g. one for housing the electronics and one for housing the battery, connected by a segment connecting section 201. According to an example embodiment, the first and second housing segments 202, 203 may be made of plastic and the segment connecting section 201 may be made of a more flexible material, such as rubber, thereby being bendable and improving portability, user comfort when the sensor is attached to the body and/or reducing motion artifacts. According to an example embodiment, the first and second housing segments 202, 203 and the segment connecting housing section 201 may be made of the same flexible material and the connecting section 201 being designed or having a shape providing improved bendable characteristics. Advantageously, the bendable segment connecting section 201 allows the first and second housing segments 202, 203 to move and have different inclination planes when the sensor device is applied on the body. According to an example embodiment, the housing segment connecting section 201 has a width W1 that is shorter than the first and second housing segments 202, 203. According to another example embodiment, the housing segment connecting section 201 forms a recess in the surface between the first and second housing segments 202, 203. Advantageously, the housing segment connecting section 201 attenuates and isolates movement forces between the first and second housing segments 202, 203.

According to an example embodiment, the housing may comprise two different sections or segments 202, 203, e.g. one for housing the electronics and one for housing the battery, connected by a middle section 201. According to an example embodiment, the two housing segments 202, 203 may be made of plastic and the middle mechanically connecting housing section 201 may be made of a more flexible material, such as rubber, thereby improving portability or user comfort when attached to the body. According to an example embodiment, the battery powers the circuit electronics and is connected with wires.

It shall be noted that other shapes and forms of the housing 201, 202, 203 of the wearable sensor unit 200 are possible without departing from the scope of the present description.

FIG. 1B shows a top view of a wearable patch unit 300 according to an example embodiment, with a shape 301, 302, 303 substantially following the shape of the housing 201, 202, 203 of the wearable sensor unit 200. The wearable patch unit 300 further comprises a flexible patch strip 309 and a connector or connection plug 310. According to an example embodiment, the patch unit is, advantageously, a disposable patch. According to an example embodiment, the patch unit segment connecting section 301 has a width W2 that is shorter than the first and second patch segments 302, 303.

FIG. 1C shows a side view of a wearable sensing device 100 according to an example embodiment, when the patch unit 300 is adhesively attached to the housing of the wearable sensor unit 200. According to an example embodiment, the wearable sensor unit comprises a receptacle connection or socket 210 for receiving the biosignals from the disposable patch unit and such that the circuit electronics can process those signals. According to an example embodiment, the patch unit comprises a connector or plug 310 that is configured to be inserted and connected with the receptacle or socket of the wearable sensor unit. According to an example embodiment, the receptacle and the plug are implemented following a Micro-USB standard. According to an example embodiment, the patch unit plug may be implemented in a Micro-USB-like or compatible standard manner but deviating from standard materials used. According to an example embodiment, the wearable sensor unit may comprise two connecting receptacles or sockets, one for receiving the patch unit plug and another for receiving an USB or Micro-USB plug for battery re/charging purposes. According to an example embodiment, the sensor unit may comprise just one socket for both connecting the circuit electronics in the sensor unit to the patch and for recharging the sensor unit battery. In this way, patient safety is increased as it ensures that the user is not able to recharge the sensor unit while wearing it. Furthermore, the fact that the wearable sensor unit can be easily detached from the patch unit allows for easy recharging of the sensor unit with a conventional USB or Micro-USB connection, while not in use.

FIG. 1D shows a bottom view of a wearable patch unit 300 according to an example embodiment, when the bottom protective liner (320 in FIG. 3I) of the patch unit is removed. The connecting plug 310 of the patch unit may be placed on any of the sides of the patch (in the example of the figure is on the left side). According to an example embodiment the plug is placed on a flexible patch strip 309 that extends from a lateral of the patch. According to an example embodiment, the flexible strip is made of the same material and forms part of the patch substrate layer (370 in FIG. 3C) and/or the foil layer (350 in FIG. 3E). According to an example embodiment, the flexible patch strip comprises electrode tracks, for example printed electrode tracks (341 in FIG. 3F) on the foil layer of the patch. According to an embodiment, such strip is defined, e.g. by dimensions and flexibility, so that it allows the plug, e.g. when the strip is bended, to enter the connection receptacle of the sensor unit.

According to an example embodiment, the connector or connection plug 310 of the patch unit is implemented in the shape and form of a Micro-USB standard plug. The connector plug however does not need to be metallic and may be made of low cost materials such as plastic or rubber. The printed electrode tracks coming out of the patch unit are built and configured in such a fashion that, when inserting this plug into a standard Micro-USB socket or receptacle, the pins are properly connected and compliant.

FIG. 1E shows a bottom view of a wearable sensor unit 200 according to an example embodiment. The bottom of the housing comprises a surface 240, 250 intended to be attached to a patch unit 300, for example by applying the first adhesive layer (380 in FIG. 3B) on that bottom surface of the housing, or vice versa. According to an embodiment, the bottom surface of the housing comprises two different surface areas for being in contact with the patch unit top adhesive layer, a first surface area 240 from the first housing segment 202 and a second surface area 250 on the second housing segment 203, which improves comfort and acquired signal quality.

Figure 2C:
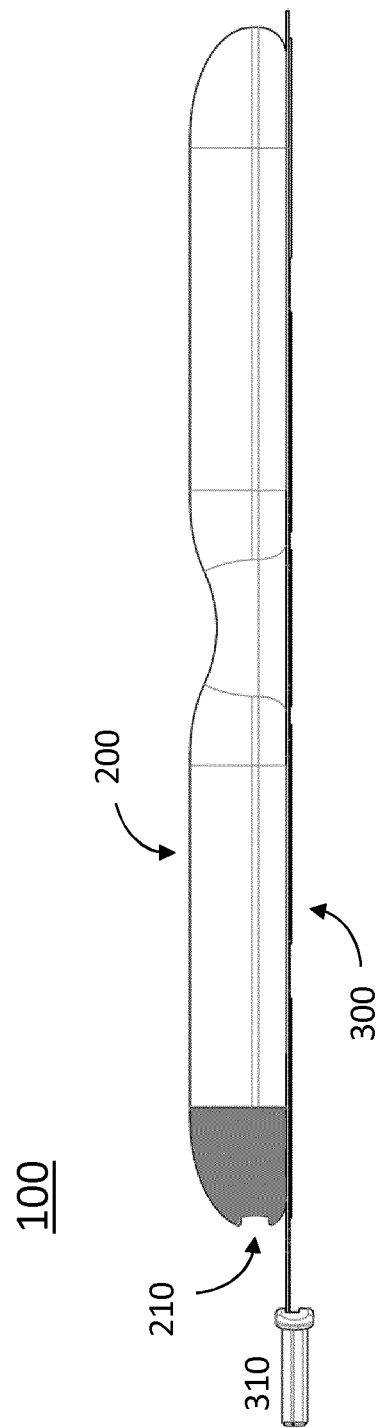
FIG. 2C shows a side view of a wearable sensing device according to another example embodiment, when the patch unit is attached to the housing of the wearable sensor unit.

FIG. 2A shows a top view of a wearable sensor unit according to another example embodiment. FIG. 2B shows a top view of a wearable patch unit according to another example embodiment. FIG. 2C shows a side view of a wearable sensing device according to another example embodiment, when the patch unit is attached to the housing of the wearable sensor unit. FIG. 2D shows a bottom view of a wearable patch unit according to another example embodiment, when the bottom protective liner is removed. FIG. 2E shows a bottom view of a wearable sensor unit according to another example embodiment.

Figure 3:
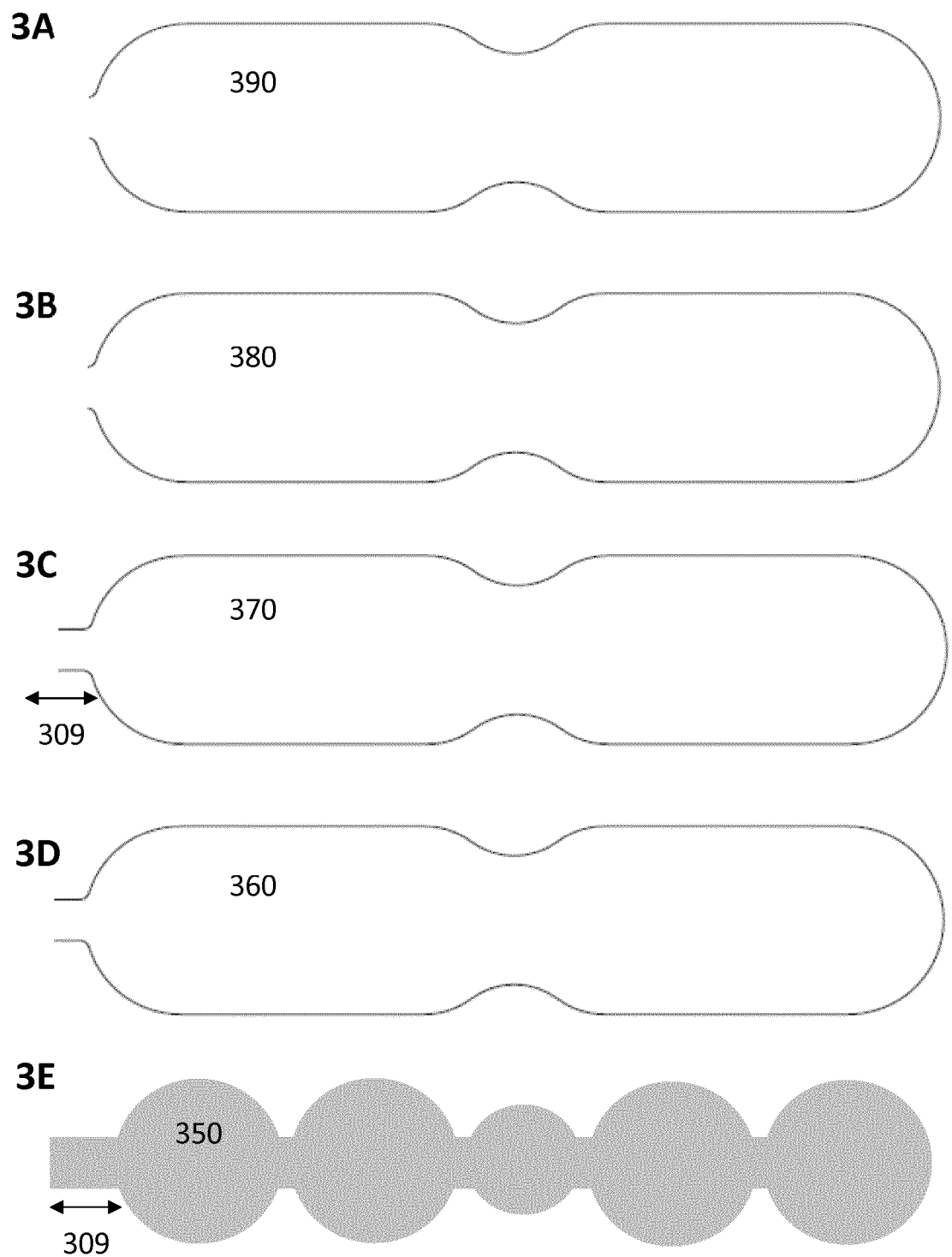
FIG. 3A shows a first protective liner layer located on top of the patch unit according to an example embodiment.
FIG. 3B shows a first layer of the patch unit with adhesive properties, located under the first liner layer, according to an example embodiment.
FIG. 3C shows a substrate layer of the patch unit, located under the first layer with adhesive properties, according to an example embodiment.
FIG. 3D shows a second layer of the patch unit with adhesive properties, located under the substrate layer, according to an example embodiment.
FIG. 3E shows a foil layer of the patch unit, located under the second layer with adhesive properties, according to an example embodiment.
FIG. 3F shows a printed electrode and conductive track layer of the patch unit, located under the foil layer, according to an example embodiment.
FIG. 3G shows an optional conductive gel layer of the patch unit, located under the printed electrode and conductive track layer, according to an example embodiment.
FIG. 3H shows an optional third layer of the patch unit with adhesive properties, located under the printed electrode and conductive track layer, according to an example embodiment.
FIG. 3I shows a second protective liner layer located at the bottom of the patch unit according to an example embodiment.

FIGS. 3A to 3I show an example implementation of a patch unit 300 from top to bottom, top meaning the layers closer to the wearable sensor unit and bottom being the layers closer to the subjects skin. FIG. 3A shows a first protective liner layer 390 located on top of the patch unit 300 according to an example embodiment. The first liner layer is removed in order to expose the first adhesive layer 380 in FIG. 3B of the patch unit when the patch unit is to be attached to the bottom of the wearable sensor unit's housing (as shown in FIGS. 1C and 2C). The first adhesive layer 380 is located on top of a substrate layer 370 in FIG. 3C and under the first top protective liner 390. In general, it shall be noted that different patch unit shapes and lengths are possible and also each of the patch unit layers herein described may vary and differ in lengths and shapes, for example, the first adhesive layer may have the same size or surface area or may present a smaller area than the top protective liner. According to another example embodiment, the adhesive layers may be implemented as a plurality of adhesive, and maybe separated, areas or having specific adhesive profiles. The substrate layer may be made of a textile or a plastic foil and advantageously provides support for the other layers in the patch unit. FIG. 3D shows a second adhesive layer 360, located under the substrate layer 370 and intended for attaching the patch unit to the subject's skin. FIG. 3E shows a foil layer 350, made of for example, PTE or TPU. The foil layer may have different shapes based on the number of electrodes needed in the patch and is adapted to receive printable electrode and conductive tracks using conventional conductive ink printing technology. FIG. 3F shows a conductive printed ink layer 340 with printed electrodes 342 and conductive tracks 341, printed on the foil layer 350. Optionally, conductive gel layer 335 in FIG. 3G, preferably a biocompatible conductive gel, may be added on the patch electrodes 342 in order to improve signal quality. Also a third adhesive layer 330 in FIG. 3H may be optionally added on specific areas of the foil layer 340, such as to improve adherence of the patch unit to the subject's skin. Finally, the patch unit comprises a second protective liner layer 320 in FIG. 3I located at the bottom. The second protective liner layer shall be removed when attaching the patch unit to the subjects skin.

Figure 4:
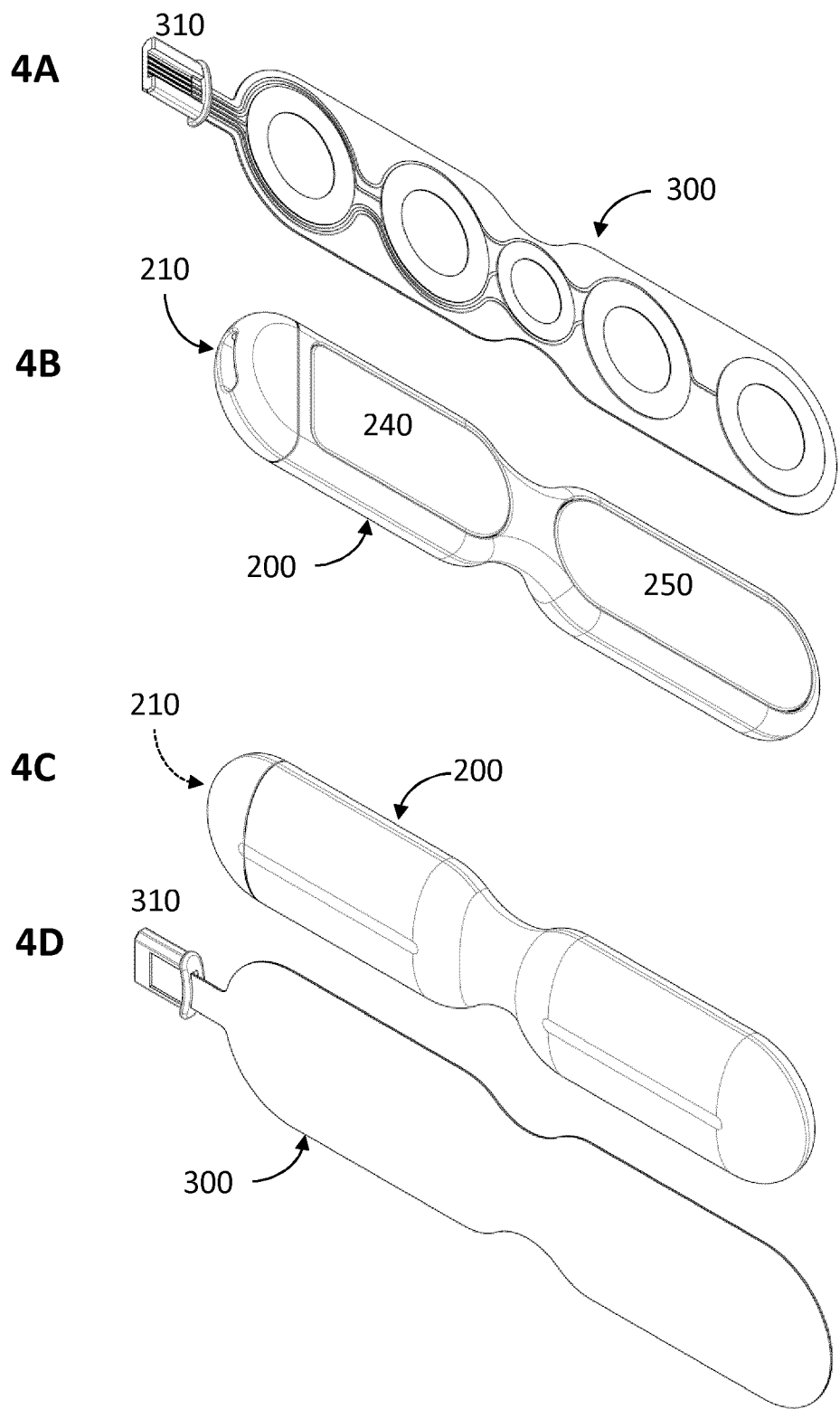
FIG. 4A shows a perspective bottom view of a wearable patch unit according to another example embodiment, when the bottom protective liner is removed.
FIG. 4B shows a perspective bottom view of a wearable sensor unit according to another example embodiment.
FIG. 4C shows a perspective top view of a wearable sensor unit according to another example embodiment.
FIG. 4D shows a perspective top view of a wearable patch unit according to another example embodiment.
Figure 5:
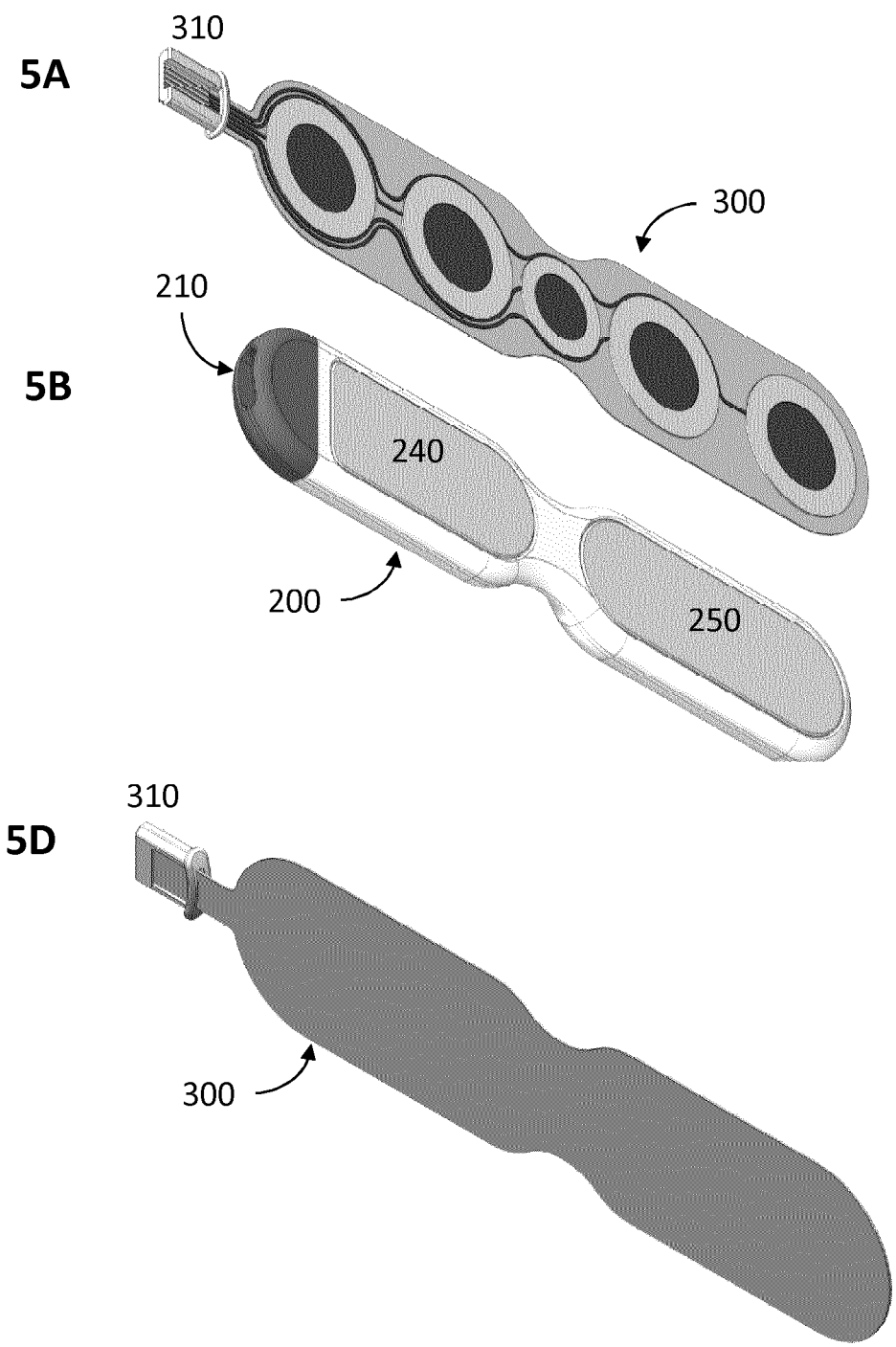
FIG. 5A shows a perspective bottom view of a wearable patch unit according to another example embodiment, when the bottom protective liner is removed.
FIG. 5B shows a perspective bottom view of a wearable sensor unit according to another example embodiment.
FIG. 5C shows a perspective top view of a wearable sensor unit according to another example embodiment.
FIG. 5D shows a perspective top view of a wearable patch unit according to another example embodiment.
Figure 5C:
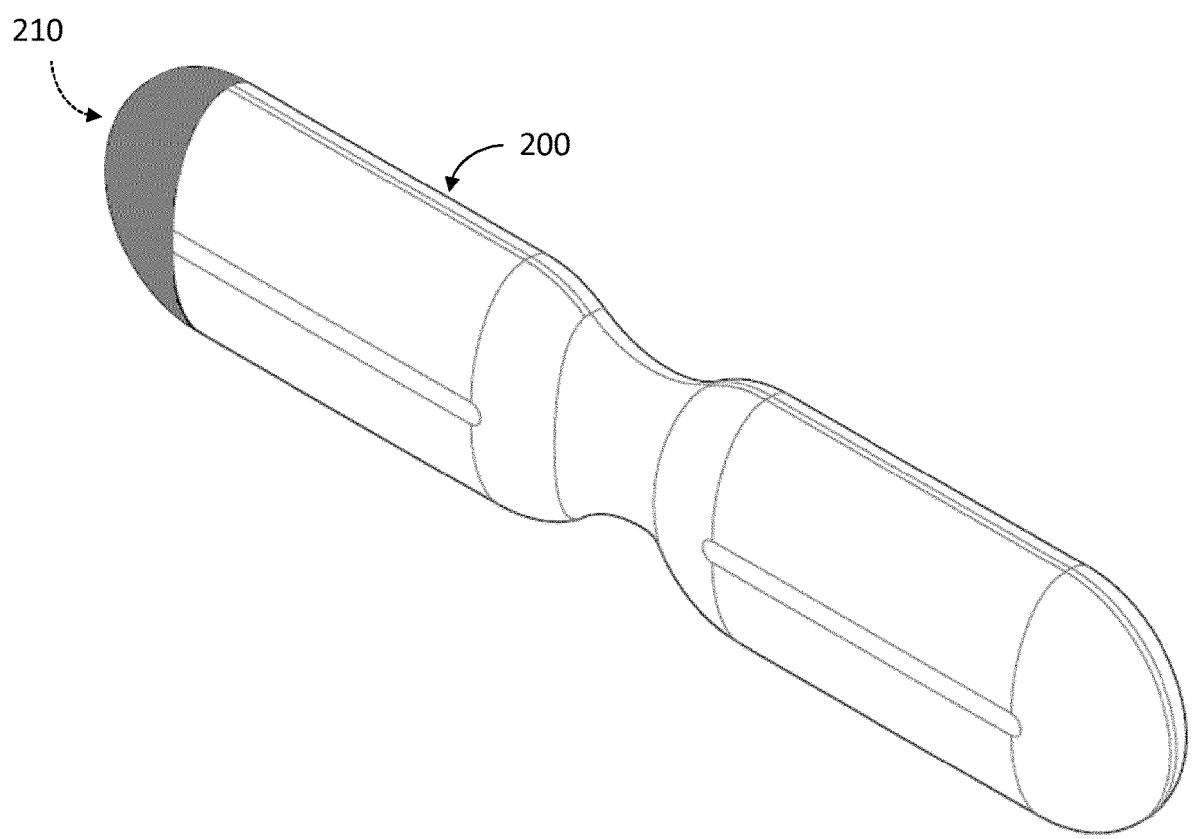

FIG. 4A shows a perspective bottom view of a wearable patch unit 300 according to an example embodiment, when the bottom protective liner is removed. FIG. 4B shows a perspective bottom view of a wearable sensor unit 200 according to an example embodiment. FIG. 4C shows a perspective top view of a wearable sensor unit 200 according to an example embodiment. FIG. 4D shows a perspective top view of a wearable patch unit 300 according to an example embodiment. FIG. 5A shows a perspective bottom view of a wearable patch unit 300 according to another example embodiment, when the bottom protective liner is removed. FIG. 5B shows a perspective bottom view of a wearable sensor unit 200 according to another example embodiment. FIG. 5C shows a perspective top view of a wearable sensor unit 200 according to another example embodiment. FIG. 5D shows a perspective top view of a wearable patch unit 300 according to another example embodiment.

Figure 6:
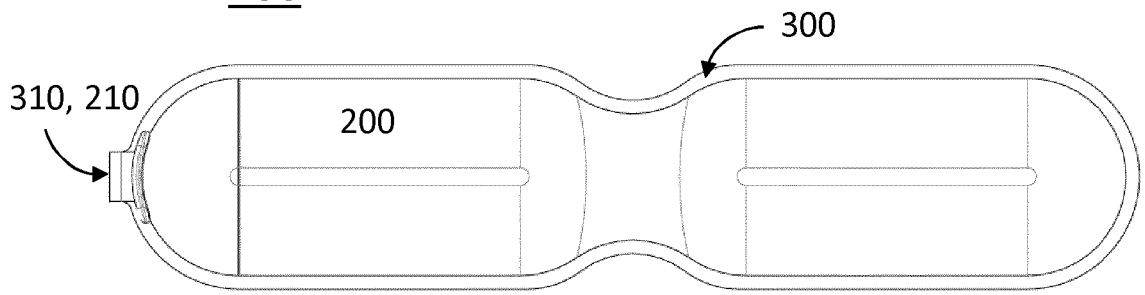
FIG. 6A shows a top view of a wearable sensing device according to an example embodiment.
FIG. 6B shows a front view of a wearable sensing device according to an example embodiment.
FIG. 6C shows a rear view of a wearable sensing device according to an example embodiment.
FIG. 6D shows a side view of a wearable sensing device according to an example embodiment, when the patch unit is attached to the housing of the wearable sensor unit and the patch unit's plug is inserted into the wearable sensor unit's socket.
FIG. 6E shows a bottom view of a wearable sensing device according to an example embodiment, when the bottom protective liner is removed.
Figure 6:
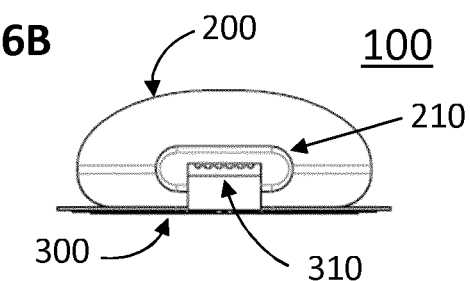
Figure 6:
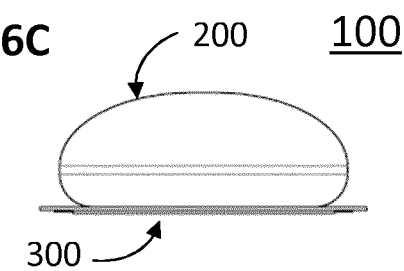
Figure 6:
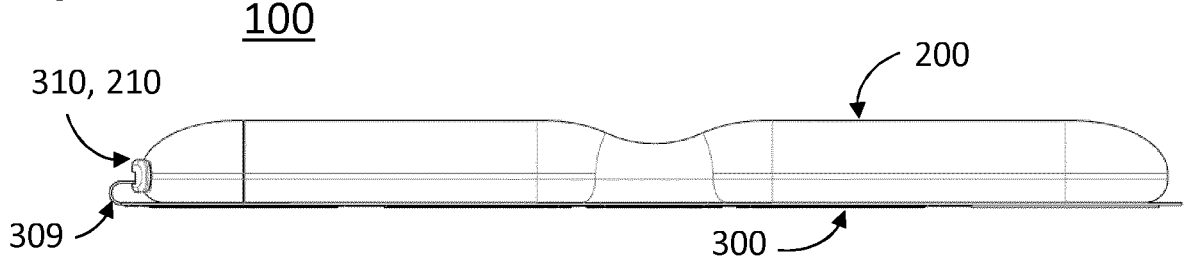
Figure 6:
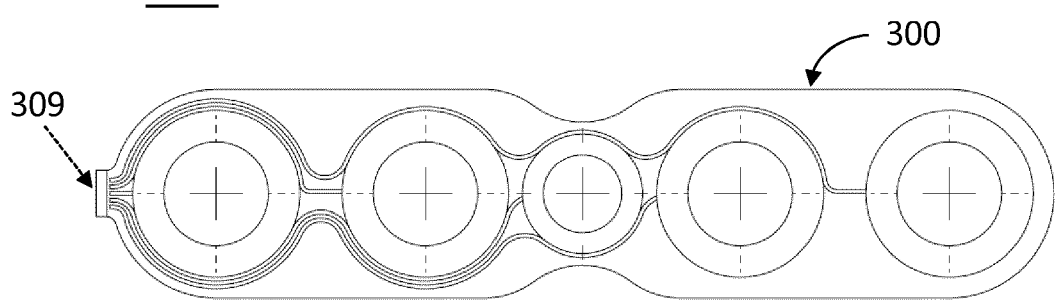
Figure 7:
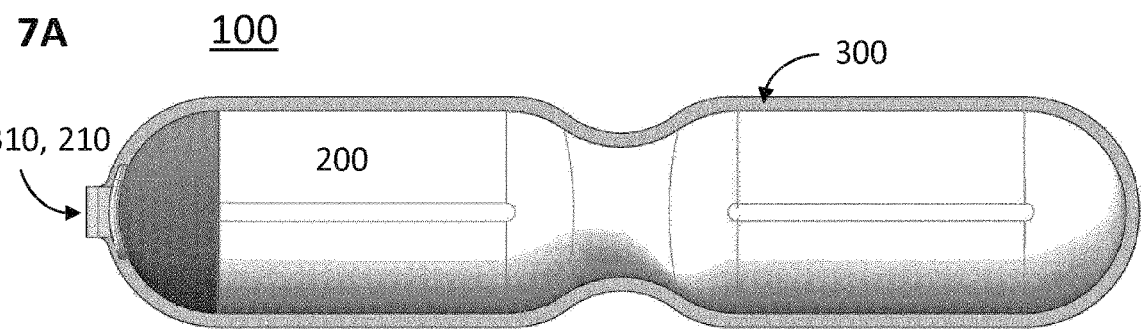
FIG. 7A shows a top view of a wearable sensing device according to another example embodiment.
FIG. 7B shows a front view of a wearable sensing device according to another example embodiment.
FIG. 7C shows a rear view of a wearable sensing device according to another example embodiment.
FIG. 7D shows a side view of a wearable sensing device according to another example embodiment, when the patch unit is attached to the housing of the wearable sensor unit and the patch unit's plug is inserted into the wearable sensor unit's socket.
FIG. 7E shows a bottom view of a wearable sensing device according to another example embodiment, when the bottom protective liner is removed.
Figure 7:
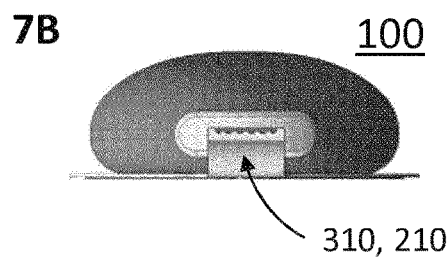
Figure 7:
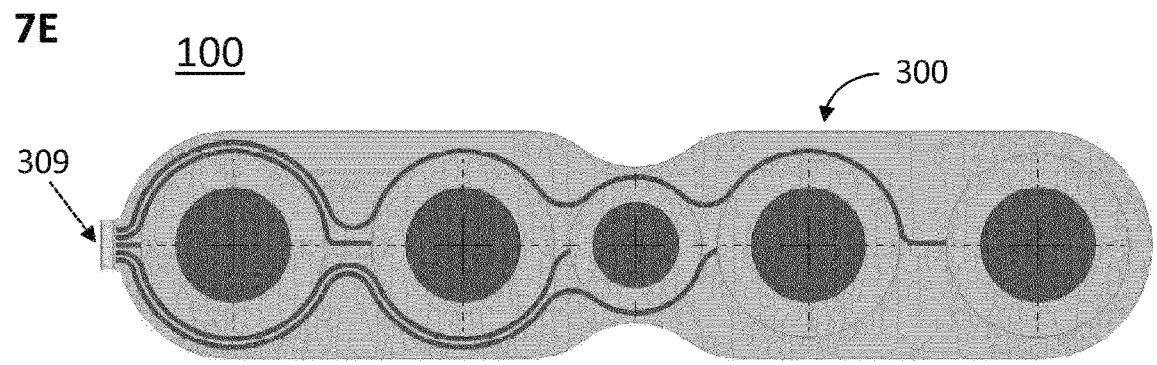
Figure 7C:
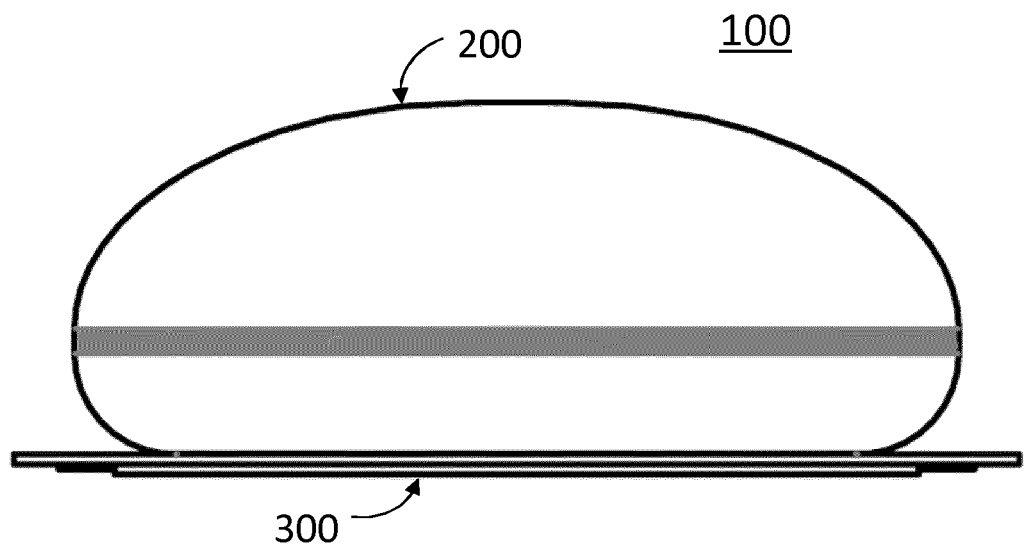
Figure 7D:
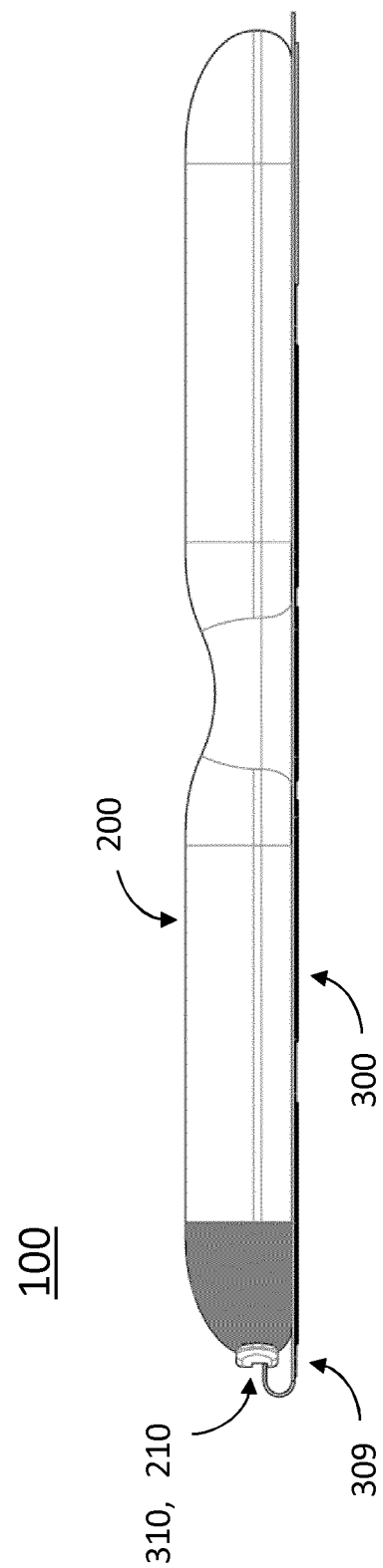

FIG. 6A shows a top view of a wearable sensing device 100 according to an example embodiment, when the path unit 300 is attached to the wearable sensor unit's housing and the connection plug 310 is inserted into the connection receptacle 210. FIGS. 6B, 6C, 6D and 6E show, respectively, a front view, a rear view, a side view and a bottom of the wearable sensing device according to FIG. 6A. The figure also shows the flexible patch strip 309, to which the connector plug 310 is attached, in a bended position. In this implementation the wearable sensing device 100 comprises five electrodes, four for biosignal measurements and one, the middle one, is used as a bias electrode.

Similarly, FIGS. 7A to 7E show a top view, a front view, a rear view, a side view and a bottom view of the wearable sensing device 100 according to another example embodiment.

Figure 8:
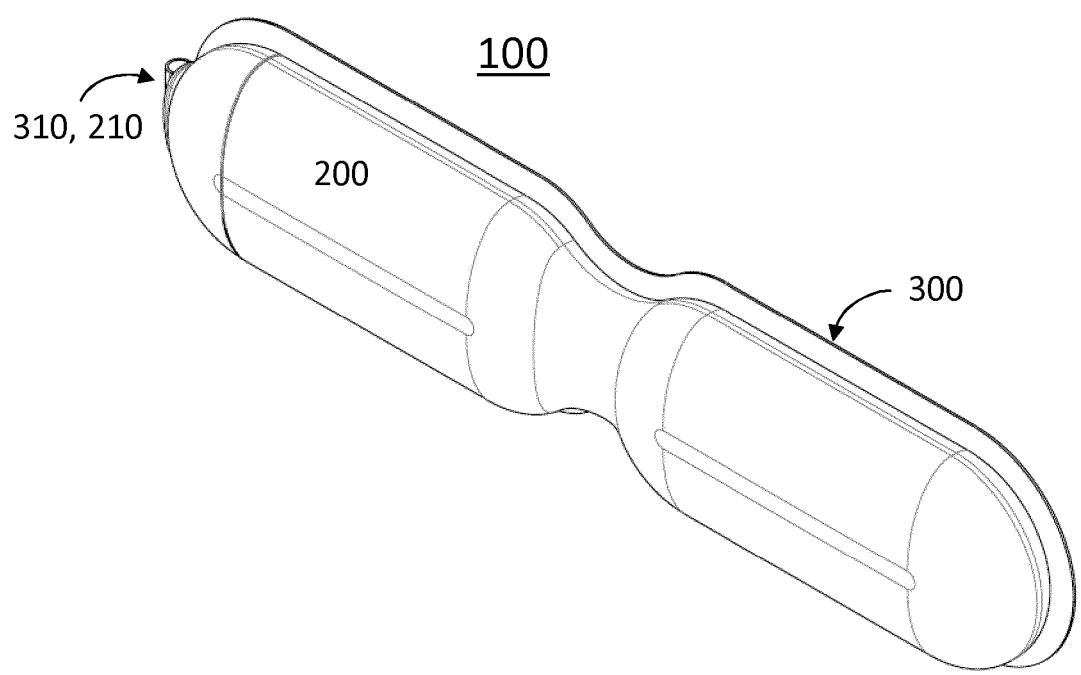
FIG. 8A shows a perspective top view of a wearable sensing device according to an example embodiment.
FIG. 8B shows a perspective top view of a wearable sensing device according to another example embodiment.
Figure 8B:
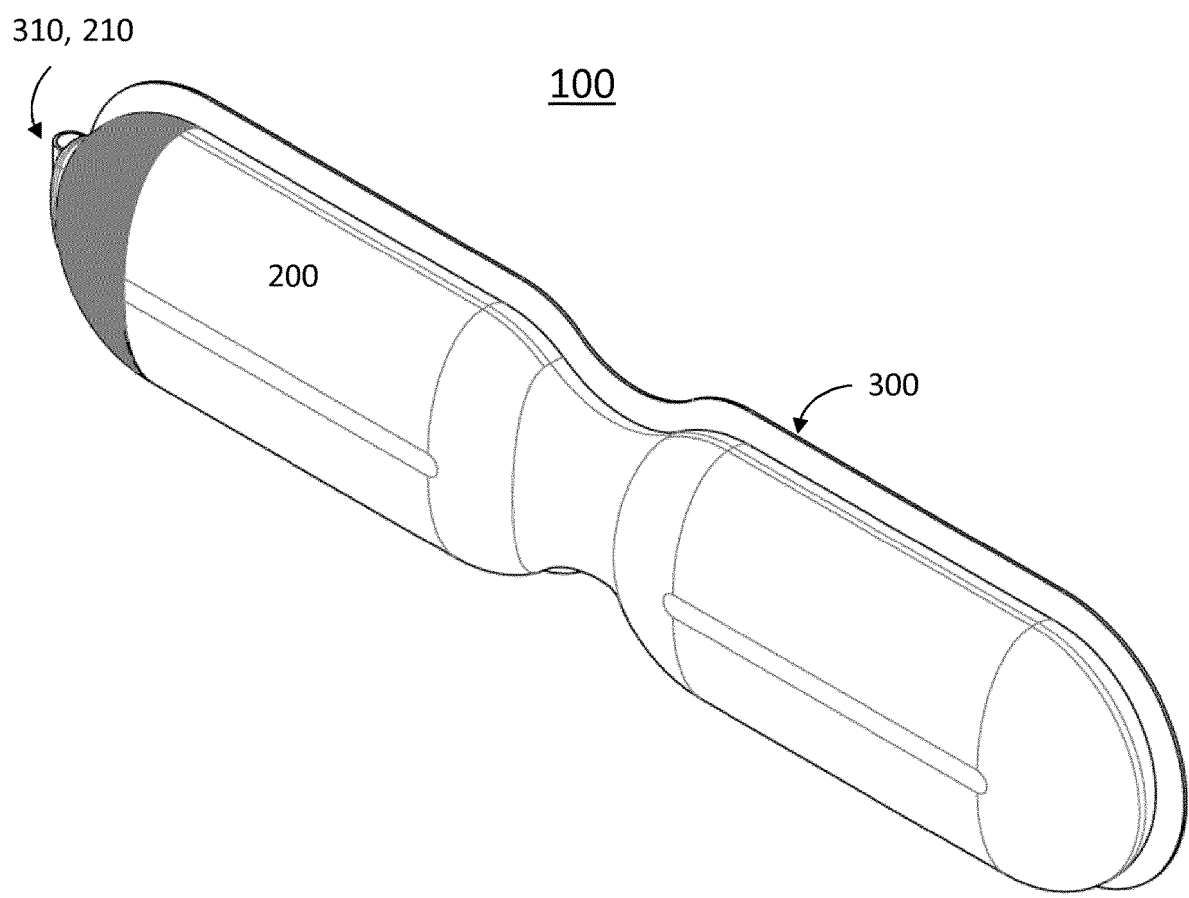

FIGS. 8A and 8B show a perspective top views of a wearable sensing device 100 according to example embodiments.

Figure 9:
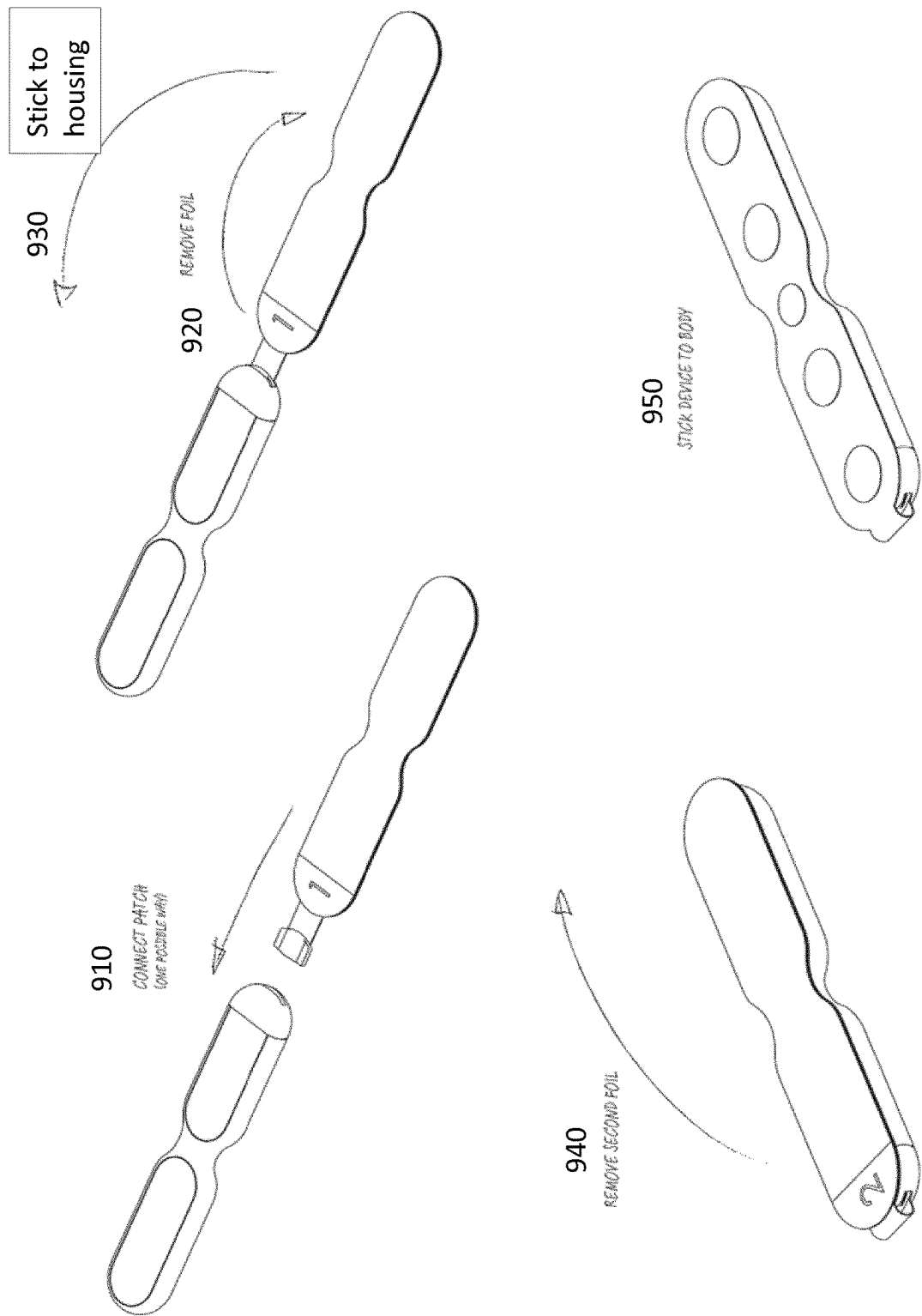
FIG. 9 illustrates a possible mounting process of the wearable sensing device according to an example embodiment.

FIG. 9 illustrates a possible mounting and attachment process of the wearable sensing device 100 according to an example embodiment. A user may first, in step 910, take a patch unit 300 and connect that unit to the wearable sensor unit 200 via the connection plug 310 (by inserting the connection plug in the socket 210). In a subsequent step 920, the user removes the first protective liner layer 390 located on top of the patch unit 300 thereby exposing the first patch adhesive layer 380. In a subsequent step 930, the user bends the patch unit, via the flexible patch strip 309, so that the adhesive layer 380 falls on the bottom surface area 240, 250 of the sensor unit's housing, and so that the patch sticks to the wearable sensor unit. In a next step 940, the user peels off the second protective liner 320 from the bottom part of the patch unit and, in a next step 950, sticks the patch on the preferred body skin location, e.g. the chest. The data acquisition may start either automatically by "lead on" detection or based on a user action to start the sensing and recording. It shall be noticed that another order of the steps above is possible, for example, attaching first the patch unit to the skin and later connect and attach the sensor unit to the patch unit.

The invention claimed is:

1. A wearable sensing device for sensing one or more physiological signals of a subject, comprising:
 a sensor unit, comprising a housing, a connection receptacle and electronic circuitry configured for acquiring one or more physiological signals received via the connection receptacle; and
 a patch unit, comprising a plurality of electrodes configured for sensing the one or more physiological signals and a patch unit connection plug connected to a flexible patch strip that extends from a lateral of the patch unit, the patch unit connection plug being connected via conductive tracks in the flexible patch strip to the plurality of electrodes; wherein
  the patch unit connection plug is configured for being connectable with the connection receptacle of the sensor unit such that the one or more physiological signals sensed by the electrodes are transmitted to the electronic circuitry of the sensor unit;
  the patch unit comprises at least one top layer and at least one bottom layer, each comprising an adhesive material, such that the at least one top layer is configured to be attachable to a surface of the housing and the at least one bottom layer is configured to be attachable to skin of the subject, and
  the patch unit connection plug is connected to the connection receptacle of the sensor unit, thereby electrically connecting the plurality of electrodes to the electronic circuitry of the sensor unit.

2. A wearable sensing device according to claim 1, wherein the sensor unit housing comprises a first housing segment, a second housing segment and a segment connecting section mechanically connecting the first and the second housing segments, the segment connecting section being bendable.

3. A wearable sensing device according to claim 2, wherein the housing segment connecting section forms a recess in the surface between the first and second housing segments.

4. A wearable sensing device according to claim 2, wherein the housing segment connecting section has a shorter width than the first and second housing segments.

5. A wearable sensing device according to claim 2, wherein the sensor unit housing comprises two separate surface areas and the at least one top layer is configured to be attachable to a first surface area of the first housing segment and to a second surface area of the second housing segment.

6. A wearable sensing device according to claim 1, wherein the patch unit comprises a first patch segment, a second patch segment and a segment connecting section connecting the first and the second patch unit segments, the segment connecting section having a shorter width than the first and second patch segments.

7. A wearable sensing device according to claim 1, wherein the flexible patch strip is made of the same material and forms part of a patch unit substrate layer.

8. A wearable sensing device according to claim 1, wherein the the top layer of the patch unit is adhered to the surface of the housing.

9. A kit of individual parts comprising:
 a sensor unit, comprising a housing, a connection receptacle and electronic circuitry configured for acquiring one or more physiological signals received via the connection receptacle;
 a patch unit, comprising a plurality of electrodes configured for sensing the one or more physiological signals and a patch unit connection plug connected to a flexible patch strip that extends from a lateral of the patch unit, the patch unit connection plug being connected via conductive tracks in the flexible patch strip to the plurality of electrodes; wherein
  the patch unit connection plug is configured for being connectable with the connection receptacle of the sensor unit such that the one or more physiological signals sensed by the electrodes are transmitted to the electronic circuitry of the sensor unit;
  the patch unit comprises at least one top layer and at least one bottom layer, each comprising an adhesive material, such that the at least one top layer is configured to be attachable to a surface of the housing and the at least one bottom layer is configured to be attachable to the skin of the subject, and
  the patch unit connection plug is configured to be connected to the connection receptacle of the sensor unit to electrically connect the plurality of electrodes to the electronic circuitry of the sensor unit.

10. A patch unit for connecting with a sensor unit as a component of a wearable sensing device for sensing one or more physiological signals of a subject, the patch unit comprising
 a plurality of electrodes configured for sensing the one or more physiological signals and
 a patch unit connection plug connected to a flexible patch strip that extends from
 a lateral of the patch unit, the patch unit connection plug being connected via conductive tracks in the flexible patch strip to the plurality of electrodes; wherein
  the patch unit connection plug is configured for being connectable with a connection receptacle of the sensor unit such that the one or more physiological signals sensed by the electrodes may be transmitted to electronic circuitry of the sensor unit;
  the patch unit comprises at least one top layer and at least one bottom layer, each comprising an adhesive material, such that the at least one top layer is configured to be attachable to a surface of the sensor unit and the at least one bottom layer is configured to be attachable to skin of the subject.

11. The patch unit of claim 10, wherein the patch unit comprises a first segment, a second segment and a segment connecting section connecting the first and the second patch unit segments, the segment connecting section having a shorter width than the first and second housing segments.

12. The patch unit of claim 10, wherein the flexible patch strip is made of the same material and forms part of a patch unit substrate layer.

13. The patch unit of claim 10, wherein the flexible patch strip is designed such that, when the connection plug is inserted into the connection receptacle of the sensor unit, the patch unit can flip over and adhere to a surface of the sensor unit.

* * * * *